US00PP35198P3

(12) United States Plant Patent
Ruter

(10) Patent No.: US PP35,198 P3
(45) Date of Patent: May 30, 2023

(54) ***ILEX* PLANT NAMED 'RUTHOL7'**

(50) Latin Name: **hybrid *Ilex* cultivar**
Varietal Denomination: RutHol7

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/882,865

(22) Filed: Aug. 8, 2022

(65) Prior Publication Data

US 2023/0045786 P1 Feb. 9, 2023

Related U.S. Application Data

(60) Provisional application No. 63/230,218, filed on Aug. 6, 2021.

(51) Int. Cl.
*A01H 5/12* (2018.01)
*A01H 6/00* (2018.01)

(52) U.S. Cl.
USPC ..... Plt./247
CPC ..... *A01H 6/00* (2018.05)

(58) Field of Classification Search
USPC ..... Plt./247
CPC ..... A01H 6/00; A01H 5/12
See application file for complete search history.

*Primary Examiner* — Keith O. Robinson

(74) *Attorney, Agent, or Firm* — Thomas Horstemeyer, LLP

(57) ABSTRACT

A new and distinct cultivar of *Ilex* plant named 'RutHol7', characterized by its upright, elliptical growth habit; a height-to-width ratio of about 2.3; grayish-purple new growth, and narrower leaves than similar *Ilex* cultivars.

2 Drawing Sheets

Figure 1:
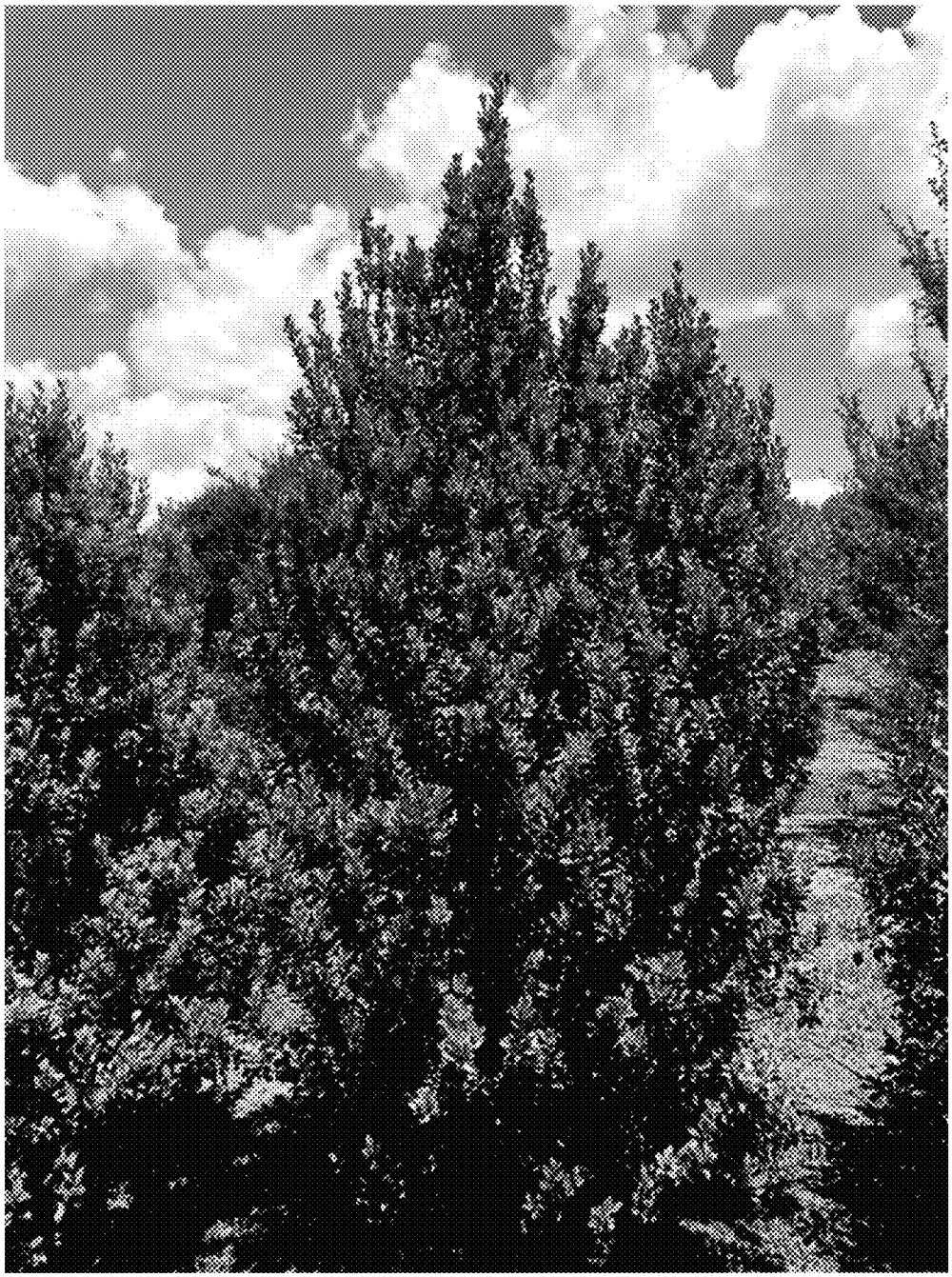

Botanical designation: Hybrid *Ilex* cultivar.
Cultivar denomination 'RutHol7'.

BACKGROUND OF THE INVENTION

The present invention relates to a new and distinct hybrid cultivar of *Ilex* (holly), and hereinafter referred to by the cultivar name 'RutHol7'.

The new *Ilex* cultivar is the product of a planned breeding program conducted by the inventor in Watkinsville, Ga. The objective of the *Ilex* breeding program is to create new plant cultivars with novel forms of growth, good cold hardiness, and resistance to damage from spider mites, insects and diseases.

The new *Ilex* cultivar 'RutHol7' is a product of a cross between the unpatented offspring of unnamed parent (*Ilex crenata* (unpatented, unnamed) x *Ilex maximowicziana* (unpatented, unnamed)) crossed with *Ilex viridis* (unpatented, unnamed). 'RutHol7' has been evaluated for container production and evaluated through trials at a horticultural farm in Watkinsville, Ga. since about 2016.

Asexual reproduction of the new *Ilex* cultivar has been continued by vegetative terminal cuttings in a controlled environment in Dearing, Ga. and Watkinsville, Ga. since about 2014. Observations of the resulting progeny have shown that the unique features of the new *Ilex* cultivar are stable and reproduced true to type in successive generations.

SUMMARY OF THE INVENTION

The new *Ilex* cultivar 'RutHol7' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Ilex* cultivar named 'RutHol7'. In combination, this combination of traits set 'RutHol7' apart from all other existing varieties of *Ilex*, including the parents, known to the inventors.

1. Columnar to upright, elliptical, vase-shaped growth habit;
2. A height: width ratio of about 2.3;
3. New growth that is grayish-purple in contrast to green mature leaves; and
4. Leaves that are broadest in the middle and narrower than *Ilex* cultivar 'RutHol6' (patent pending).

Plants of the 'RutHol7' differ from the most similar *Ilex* cultivars based on at least some of the above characteristics. The maternal parent is no longer available, so direct comparison is not possible. Neither grandparent cultivar, nor parent *Ilex virdis* exhibits the grayish-purple new growth of 'RutHol7'. 'RutHol7' also has a greater leaf aspect (about 45-65°) than grandparent *Ilex viridis* (about 15-35°). 'RutHol7' has a narrower, more columnar growth habit and narrower leaf width than sister cultivar 'RuHol6' (patent pending). 'RutHol7' can also be compared to *Ilex crenata* 'MAD-IC-I' (U.S. Plant Pat. No. 32,035), which has leaves that are crenate and cupped, as compared to the greyish-purple new growth and wider ultimate leaves with serrulate margins of 'RutHol7'. 'RutHol7' is also faster growing with a greater mature height and more elliptical overall shape than 'MAD-IC-I'.

BRIEF DESCRIPTION OF THE PHOTOGRAPHS

The accompanying colored photographic illustrations show the overall appearance and distinct characteristics of the new cultivar of *Ilex* 'RutHol7' showing the colors as true as possible. Colors in the photographs may differ slightly from the color values cited in the detailed botanical description. The photographs were taken of plants grown outdoors in Watkinsville, Ga. in May of 2021 and are described in the captions below.

The photograph labeled FIG. 1 depicts a full view of a typical 6-year-old 'RutHol7' plant showing the symmetrical, ovoid growth habit.

Figure 2:
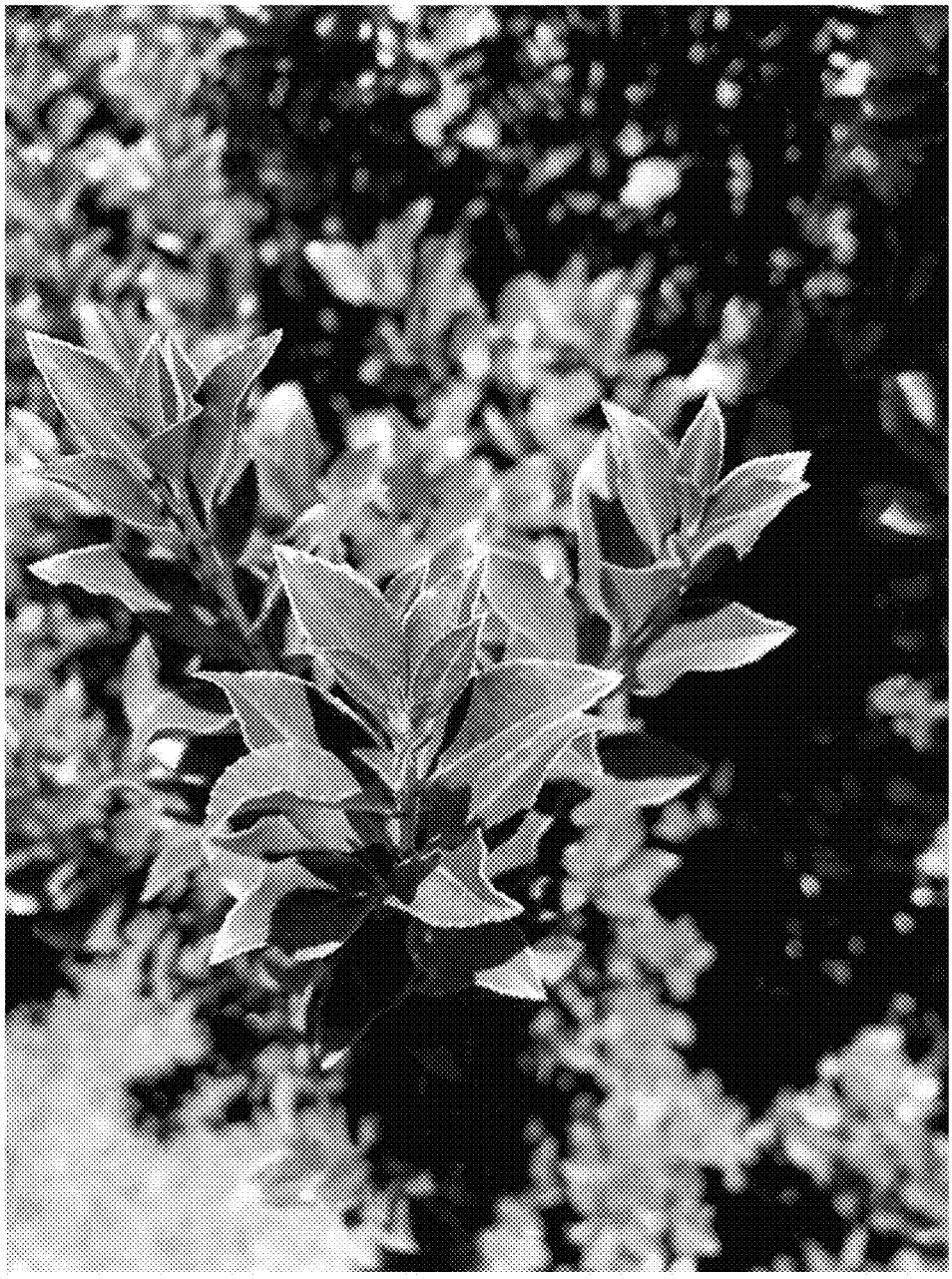

The photograph labeled FIG. 2 depicts a close-up view of some branches of a typical 6-year-old 'RutHol7' plant showing the grayish-purple new growth.

DETAILED BOTANICAL DESCRIPTION

The following traits have been consistently observed in the original plants of the new 'RutHol7' and in asexually propagated progeny grown in Watkinsville, Ga., and, to the best knowledge of the inventors, their combination forms the unique characteristics of the new variety *Ilex* 'RutHol7'.

Throughout this specification, color names beginning with a small letter signify that the name of that color, as used in common speech, is aptly descriptive. Color names beginning with a capital letter designate values based upon The R.H.S. Colour Chart, $6^{th}$ edition published by The Royal Horticultural Society, London, England in 2015, except where general terms of ordinary dictionary significance are used.

The aforementioned photographs and following observations, measurements, and values describe plants of the *Ilex* cultivar named 'RutHol7'. Data were collected from a horticulture farm in Watkinsville, Ga. from 6-year-old plants. The average low temperatures ranged from about 15° F. to 30° F. in the winter and about 90° F. to 100° F. in summer.

Botanical classification: *Ilex* 'RutHol7'.

Commercial classification: Ornamental, landscaping.

Parentage: Cross between (*Ilex crenata* (unpatented) x *Ilex maximowicziana* (unpatented)) x *Ilex viridis* (unpatented).

Growth and propagation:

- *Propagation type*.—Vegetative terminal cuttings.
- *Growth rate*.—Moderate.
- *Root description*.—Typically about 5-10 roots arising from the base of the cuttings.
- *Rooting habit*.—Moderate.

Plant description:

- *Habit*.—Of 6-year-old plant in field — upright, elliptical shrub that can have a columnar, vase-shaped form.
- *Usage*.—Various uses, including landscaping, ornamental, container, border, hedge, and mass planting.
- *Vigor*.—Moderate to vigorous.

Size of 6-year-old plant:

- *A. Height*.—From soil level to top of plant, about 108 inches.
- *B. Width* (*at widest portion*).—About 48 inches.
- *C. Ratio* (*h:w*).—About 2.3.

Branch/stem (terminal tuft):

- *A. Quantity*.—Numerous, with an average of about 18 main branches and about 40-50 lateral branches per main branch.
- *B. Length*.—About 4-22 cm.
- *C. Base diameter*.—About 2 mm at about 15 cm from tip.
- *D. Branch habit and angle*.—Dense and upright with a branch angle of about 45-65° from center.
- *E: Odor* (*of bruised stem*).—None detected.
- *F. Internode length*.—About 2-5 mm.
- *G: Color* (*R.H.S.*).—Upper side — Yellow-Green 144A.
- *H: Strength of lateral branches*.—Strong.
- *I: Texture/pubescence*.—Moderately hispid.
- *J: Shape*.—Ridged, 5-sided.
- *K: Lenticles*.—Absent.

Leaf:

- *A. Leaf type*.—Simple.
- *B. Color* (*R.H.S.*).—Upper surface — emerging leaves are Greyed-Purple 187A; mature leaves are Green NN137A, lower surface — emerging leaves are Greyed-Purple 187A; mature leaves are Yellow-Green 146B.
- *C. Mature size* (*l×w*).—About 8-9 cm×about 2-2.5 cm.
- *D. Apex*.—Acute.
- *E. Base*.—Cuneate.
- *F. Margin*.—Serrulate.
- *G. Shape*.—Elliptical, reflexed, broadest in the middle of leaf.
- *H. Lobes*.—Absent.
- *I. Pubescence*.—Smooth, no pubescence.
- *J. Arrangement on stem*.—Alternate.
- *K. Venation*.—Pinnate with coloration of both upper and lower surfaces Yellow green 145A.
- *L. Texture*.—Both upper and lower surface — leathery.
- *M. Odor when crushed*.—None detected.
- *N. Aspect*.—About 45-65°.
- *O. Leaf number*.—Average of about 1.3 per cm/stem.

Petiole:

- *A. Length*.—About 4 mm.
- *B. Shape*.—Oval.
- *C. Color*.—Yellow-Green 144A.
- *D. Texture/pubescence*.—Slightly hispid.
- *E. Diameter*.—About 1 mm.

Inflorescence:

- *A. Type*.—Solitary in clusters of 1 to 4; dioecious.
- *B. Peduncle*.—Color — Yellow Green 144A; length — about 5-7 mm.
- *C. Size*.—Height — about 5-6 mm; diameter — about 14-16 mm.

Flower:

- *A. Number per inflorescence/stem*.—1 female.
- *B. Axillary or terminal*.—Axillary.
- *C. Symmetry*.—Regular; Attitude: superior.
- *D. Size* (*l×w*).—About 3 mm by about 4 mm.
- *E. Fragrance*.—None detected.
- *F. Bud*.—Size (L×W) — about 2 mm by about 2 mm; shape — oval-rounded; color: Yellow Green 144C; texture/pubescence — smooth, no pubescence.
- *G. Petals*.—Number — 4; size (L×W) — about 2 mm×about 2 mm; shape — ovate-rounded; apex — round; base — truncate; margin — smooth, entire; color at peak bloom — Yellow-Green 144C with Green-White 157A around margins; texture — smooth, no pubescence; arrangement — symmetric.
- *H. Pedicels*.—Color — Yellow Green 144A; texture/pubescence — very slightly and sporadically pubescent; length — about 3 mm; aspect — erect; strength — strong.
- *I. Sepals*.—Number — About 4; size (L×W) — about 1.0 mm×1.5 mm; shape — acuminate; texture/pubescence — no pubescence; color — Yellow-Green 144A; apex — rounded to mucronate; base — connate; margin — entire.

*J. Stamens*.—Number — about 4, non-functional; anther — missing; no pollen.

*K. Pistils*.—a. number — about 4; stigma, style and ovary are all fused b. stigma — ovate, Orange-White 159D, smooth texture, no pubescence; c. style — about 1 mm×0.5 mm (L×W), Orange-White 159D, smooth texture, no pubescence d. ovary — about 2×1.5 mm (L×W), Yellow Green 146A, smooth texture, no pubescence, position is hypogynous

*L. Lastingness*.—About 2-3 days.

Fruit:

*A. Type*.—Berry-like drupe.

*B. Immature fruit*.—Size (L×W) — about 3 mm by about 3 mm; smooth texture; color — Yellow Green 144A.

*C. Mature fruit*.—Size (L×W) — about 5 mm by about 4-5 mm; smooth texture; color — Black 202A; shape — globose.

*D. Quantity*.—About 2-3 per infructescence.

*E. Time of maturity*.—October-November.

Seed:

*A. Number per fruit*.—About 4.

*B. Size* (*l*×*w*).—About 5 mm by about 3 mm.

*C. Color*.—Greyed Orange 165D.

*D. Shape and texture*.—Ovoid with striated surface texture.

Weather/temperature tolerance: Not fully determined. Plants of the new *Ilex* have been grown in USDA zone 8a. Parental species have survived down to −5° F. with no damage in Blairsville, Ga. Parent species *Ilex viridis* shows foliar yellowing (photoinhibition) in the winter in Watkinsville, Ga.

Disease/pest resistance: To date, plants of the new *Ilex* have not been observed to have notable disease/pest resistance as compared to other *Ilex* cultivars grown under similar conditions.

It is claimed:

1. A new and distinct cultivar of the *Ilex* plant named 'RutHol7' as illustrated and described herein.

* * * * *